United States Patent [19]
Voss

[11] 4,157,456
[45] Jun. 5, 1979

[54] AUDIOMETER

[75] Inventor: Rainer Voss, Oststeinbek, Fed. Rep. of Germany

[73] Assignee: U.S. Philips Corporation, New York, N.Y.

[21] Appl. No.: 877,826

[22] Filed: Feb. 15, 1978

[51] Int. Cl.$^2$ ............................................. H04R 29/00
[52] U.S. Cl. ................................... 179/1 N; 179/1 P
[58] Field of Search ........................................... 179/1 N

[56] References Cited
U.S. PATENT DOCUMENTS 3,808,354  4/1974  Feezor et al. ........................ 179/1 N Primary Examiner—Kathleen H. Claffy
Assistant Examiner—E. S. Kemeny
Attorney, Agent, or Firm—Thomas A. Briody; William J. Streeter; Bernard Franzblau

[57] ABSTRACT

An audiometer that automatically produces test tones of predetermined duration whose frequency and level are changed in accordance with a programme. The persons being examined actuate a switch or the like each time that a test tone is perceived and the parameters of said test tone (frequency and level) are stored in a memory. Thus, evaluation becomes very simple. Furthermore, steps have been taken to measure the background level in the test room and to ensure that the test tone is repeated when the background level exceeds a maximum value during the time that the test tone is produced.

11 Claims, 1 Drawing Figure

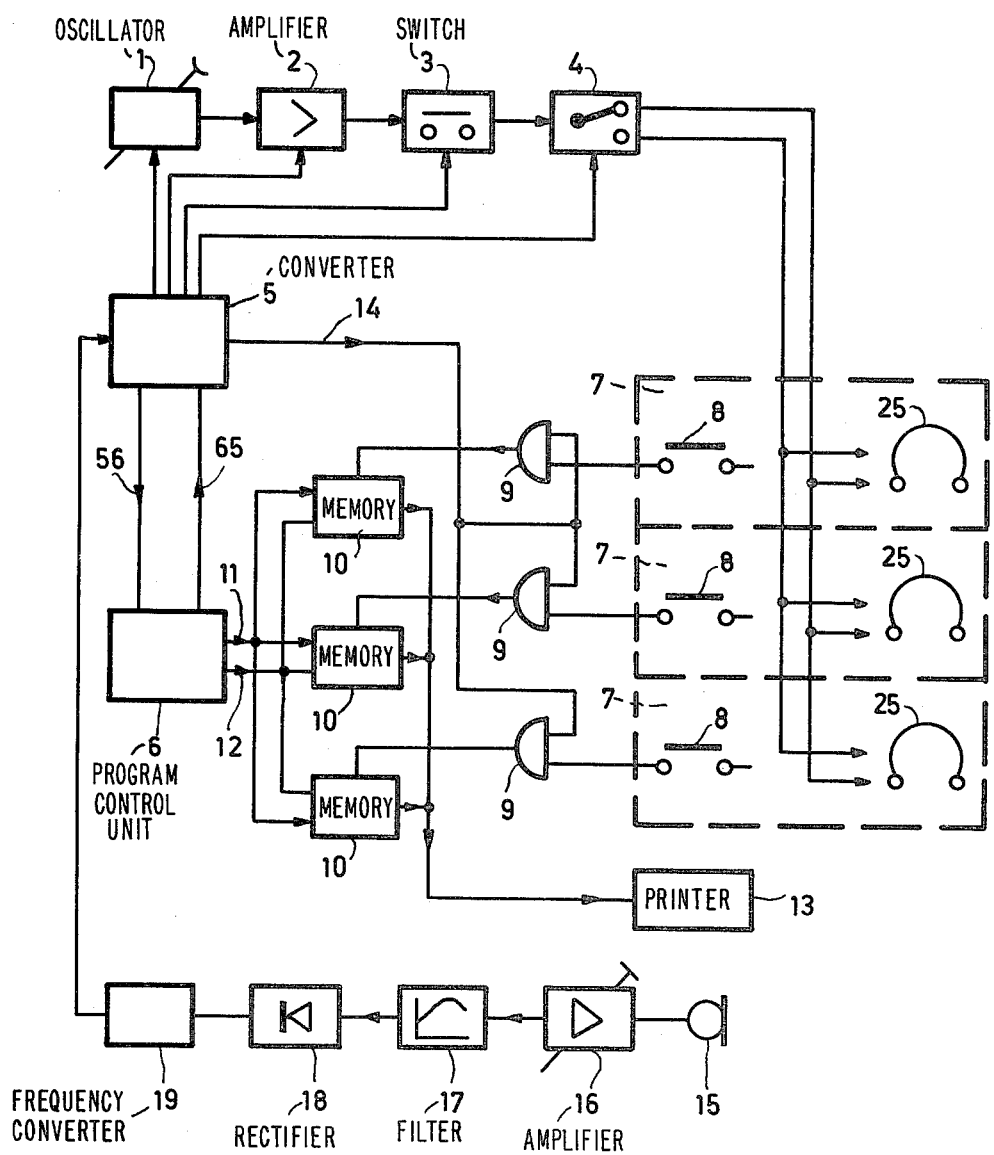

AUDIOMETER

The invention relates to an audiometer which automatically generates a series of test tones of predetermined duration, different frequency and/or different levels in accordance with a programme. The audiometer also has one or more test stations which each comprise a reproducing device and an actuating element for recording the test tones which have been perceived.

Such an audiometer is known from United Kingdom Pat. No. 1,348,197. During a predetermined time interval (=presentation time) this audiometer produces a test tone whose frequency and level are constant during the presentation time. This tone is presented to all of the reproducing devices (headphones) at the same time. When the test tone is perceived, the subject actuates a push-button which initiates a recording operation for the relevant test station and for the relevant test tone. After a pause a different test tone with the same presentation time but with a different frequency and/or different level is produced so that at the end of the examination procedure the ability to hear can be determined on the basis of a series of test tones each time of a different frequency and/or different level.

The test tones being perceived are recorded by means of a so-called stylus unit. This stylus unit has a stylus for each test position, upon whose actuation the tone which is then perceived is marked in an audiogram corresponding to the test station. In this audiogram the level of the test tone being perceived is plotted as the ordinate and its frequency as the abscissa. For a new test tone of a different level the stylus unit is bodily moved in the direction of the abscissa of the audiogram chart (for a test tone of a different frequency it is moved in the direction of the ordinate) so that the individual styli are then each positioned above that point of the associated audiogram chart which is representative of the level and the frequency of the test tone.

The stylus unit is a complicated vulnerable part of the audiometer. Extension of the number of test stations is possible, but only with considerable difficulty. Evaluation of the large number of audiogram charts employed for a series examination with such an audiometer is time-consuming.

It is an object of the invention to provide an audiometer which is less vulnerable, which is more flexible with respect to the number of test stations, and which simplifies the evaluation procedure.

According to the invention this problem is solved, starting from an audiometer of the type mentioned in the preamble by providing a digital electronic memory or a part of such a memory having a write input or an information input allocated to each test station. A digital signal corresponding to the level or frequency of the test tone is applied to the information and/or the address inputs of the memory. The memory write or information input associated with a test station can be controlled by the actuating element located at the test station and an output device is provided for the read-out of the signals stored in the memories or the memory.

Storage is possible in different ways:

(a) To the information input a digital signal is applied which corresponds to the frequency and the level of a test tone. The write input can be controlled by the actuating element so that the digital signal which appears on the information input is stored when the subject perceives the test tone and actuates the actuating element.

(b) To the address input of a memory an address is applied which corresponds to a test tone parameter to be changed, preferably the frequency, and to the information input a digital signal is applied which corresponds to the other parameter, i.e. the test tone level. When the subject perceives the test tone and operates the actuating element, the test tone level is written into the memory in the address assigned to the test tone frequency. This write-in method requires a low storage capacity and renders satisfactory evaluation possible.

(c) A digital signal, which characterizes the level and frequency of the test tone, is applied to the address input only. The actuating elements should then be connected to the information inputs of the digital memory. When they are actuated by the subject a binary signal ("1" or "0") is written into the memory in the address corresponding to the frequency and the level of the test tone.

The use of digital signals which characterize the test tone frequency and level constitutes no significant additional complication because such signals must be available anyway for controlling the frequency and the attenuation or gain of the tone generator.

Audiograms thus obtained can be evaluated automatically in a particularly simple manner. As an example, the hearing thresholds thus determined for the different frequencies may be compared with the (equally stored) "normal values" for a person of the same age, and—in addition to the absolute values—the difference in level between the thresholds of hearing of the subject and a person with normal hearing can be read out with the output device, for example, a printer.

For audiometric measurements correctly sound-proofed rooms are necessary, which in virtually all cases can be realized only with substantial cost. In the case of mobile devices, for which the audiometer in accordance with the invention is particularly suitable, this is particularly difficult or in many cases impossible for reasons of bulk and weight. Despite the use of acoustic caps which damp extraneous sounds, it may therefore frequently happen that audiometric test results are invalidated by background noise because the subjects do not hear the test tone when there is background noise or mistake the background noise for the test tone to be perceived.

In accordance with a further embodiment of the invention these erroneous results can be avoided in that the test room is provided with a microphone for measuring extraneous sound, means are provided for the formation of a signal which corresponds to the average value of the microphone signal level during the presentation time of the test tone, and that depending on the difference in level between the extraneous sound and the test tone the test tone can be repeated. The signal which then causes the test tone to be repeated may then simultaneously suppress the signal produced by the actuating elements or may cancel the values stored in the memory during the extraneous sound so as to prevent any incorrect results. Instantaneously occurring extraneous sound effects, which mask a test tone which has just been given, thus cause the test tone to be repeated, namely a predetermined number of times or so often that the difference in level between the test tone and the room level has reached a permissible value. The permissible value of the difference between the test tone level and the extraneous sound level depends on the quality of the acoustic caps fitted around the headphones and may be adjusted in accordance with their acoustic damping values. An audiometer thus equipped may then also be employed in less satisfactorily sound-proofed rooms.

The invention and further advantages thereof now will be described in more detail with reference to the drawing.

The tone generator comprises an oscillator 1 with a frequency which is adjustable in steps. The oscillator output signal is applied to a switch 3 via an amplifier 2 whose gain or attenuation is electronically adjustable in steps. The opening time of said switch determines the intervals between two test tones and the closing time corresponds to the duration of a test tone, i.e. the presentation time. The output of the switch 3 is connected to a plurality of headphones 25 via a change-over switch 4, via which headphones—depending on the position of the switch 4—the test tone can be applied at option to the left or the right or both ears of the subject.

The oscillator 1, the amplifier 2, the switch 3 and the change-over switch 4 are controlled by a converter 5, which in its turn receives instructions from a programme control unit 6 via the line 65 and supplies information to the programme control unit via the line 56. For controlling the oscillator 1 and the attenuation of the amplifier 2 the converter 5, in known manner, may comprise a shift-register with a number of register cells corresponding to the number of frequency and damping stages respectively (compare United Kingdom Pat. No. 1,348,197). However, there may also be provided a coding device which re-codes the, for example, binary-coded signal supplied by the programme control unit 6 and corresponding to the test-tone frequency and level in such a way that only one of its outputs, whose number corresponds to the number of frequency and level stages respectively, carries a specific digital signal ("1" or "0") and renders a resistor in the oscillator 1 or amplifier 2, which resistor determines the frequency or level respectively, operative. In addition to the headphones 25 the test stations 7—the drawing shows only three stations but there may be provided any arbitrary number of other stations—each comprise an actuating element in the form of a key switch 8 to be actuated by the subject being tested when a test tone is perceived. So far the audiometer is essentially similar to the device shown in the aforesaid United Kingdom patent.

The switches 8 are each connected to the write inputs of memories 10 via an AND-circuit 9. The information inputs of the memories 10 are connected to the programme control unit 6 via line 11 and their address inputs via line 12. Via the line 11 the programme control unit supplies an information signal which characterizes the instantaneous level of the test tone and via the line 12 an address signal which characterizes the instantaneous frequency of the test tone. For the sake of simplicity the drawing shows only one information line 11 and one address line 12, but in practice more lines are required. These signals are also applied to the converter 5 which changes the level and the frequency accordingly. If a switch 8 is actuated by one of the subjects when a test tone is perceived, the information signal characterizing the test tone level on the line 11 is stored in the memory 10 associated with the actuated switch at the address determined via the line 12 and characterizing the frequency (and the ear being examined—right, left).

Storage of the test tones which have been perceived may also be effected as described in the introduction under (a) or (c). It is essential only that the values stored in the memory 10 unambiguously correspond to the frequency and the level of each test tone being perceived. Instead of a separate memory for each test station there may also be provided a common memory for all test stations. The output signals of the AND-circuits 9 should then be stored temporarily and read out sequentially.

The outputs of the memories 10 are connected to an output device, for example in the form of a printer 13, and the results can be printed—time sequentially—on said printer. The programme control unit 6, the memories 10, the functions of the gates 9 and the printer may be realized jointly by means of a commercially available calculator. The programme control unit 6, however, can also be designed on the basis of a microprocessor, which can then also perform the functions of the AND-gates 9.

If one of the switches 8 is not actuated during a test tone (i.e. if the switch remains open) or after a specific comparatively short time interval after the test tone has been produced, but later, before the next tone is produced, it may be assumed that the subject has not perceived the test tone although the switch 8 has been actuated. In order to prevent storage of this test tone a signal may be applied via a line 14, which signal blocks all AND-gates for a specific time after each test tone has been produced and does not release them until the next test tone is produced. This signal may for example be generated by the converter 5 which switches the test tone on and off. However, instead of this, write instructions which arrive too late (i.e. a specific time after the test tone has sounded) may be added to the contents of another storage location in the relevent memory, for which purpose the signals on the address and the information inputs of the memories should also be changed during these time intervals. The contents of this storage location at the end of an audiometric test then indicates how many times the subject has responded incorrectly.

When the test room is not satisfactorily soundproofed, in particular when a large number of persons are examined in said room at the same time, it may happen that a test tone is masked by extraneous sound or that the subject erroneously takes the extraneous sound for the test tone. Such erroneous responses cannot be entirely prevented by acoustic caps which are mounted over the measuring headphones 25 because the acoustic damping values are naturally limited.

Therefore, in accordance with the invention, an average value of the extraneous sounds during the presentation time of a test tone is formed, and the test tone is repeated when the difference between the level of the test tone and the extraneous sound exceeds a predetermined value—which preferably depends on the damping values of the acoustic caps—(i.e. when the sound pressure of the test tone is a specific factor greater or smaller than the sound pressure of the extraneous sound). For this purpose there is provided a microphone 15 whose signal is amplified by an amplifier 16, which preferably has a variable gain, and applied to a filter 17 whose frequency response substantially corresponds to the frequency response of the hearing of a person with normal hearing. The output signal of this weighting filter 17 is rectified in a rectifier 18 and applied to a frequency converter 19, whose output signal has a frequency which is proportional to the amplitude of its input signal. The output pulses of converter 19 are counted by a counter, not shown, in the converter 5 during the presentation time, i.e. while the switch 3 is closed. Thus, the count at the end of the presentation time is a measure of the extraneous sound during the presentation time. When the difference between the extraneous sound thus measured and the test-tone level determined by the programme control unit via the line 65 exceeds a predetermined value, the programme control unit is made to repeat the instruction associated with said test tone via the line 56. The test tone may then be repeated a predetermined number of times or until the difference between the test tone and the extraneous sound has reached a permissible value. Suitably, the contents of the storage location corresponding to the test tone is then erased in order to avoid incorrect registrations. It is alternatively possible to measure the background level outside the presentation time of the test tone and to repeat the measurement until the difference between the extraneous sound level and the test tone level exceeds the predetermined value, after which the test tone—by closure of the switch—is presented to the subject. Preferably, the two possibilities are combined. Thus, when the background level during the measurement is too high, the extraneous sound measurement is repeated until the measured background level has decreased to the permissible value and it is not until then that the test tone is repeated. The interruption of the series of test tones, which are preferably produced at variable time intervals, in the case that the permissible background level is exceeded may be signalled to the subjects by optical or other signals.

It is not necessary to convert the extraneous sound level into a digital signal whose frequency depends on the level. It is for example possible to vary the gain of the amplifier 16 by means of the converter in a sense opposed to that of the gain of the amplifier 2 so that the product of the two gain factors remains constant. In this case an extraneous sound level, which bears a specific ratio to the effective-signal level, results in a direct voltage at the output of the rectifier 18 which is independent of the effective-signal level. Whether said threshold value is exceeded can simply be detected by means of a threshold switch. Similarly, a signal which is proportional to the amplitude of the output signal of the amplifier 2 may be compared with the output signal of the rectifier 18 and the test tone may be repeated when the output signal of the rectifier 18 is predominant.

What is claimed is:

1. An audiometer system for digitally recording data for one or more audiometric patients comprising, a plurality of test stations each of which comprises a reproducing device and an actuating element for recording test tones which are perceived, means common to said plurality of test stations for automatically generating for said plurality of test stations a series of test tones for predetermined duration, different frequency and/or different levels in accordance with a programme, said tone generating means being independent of any control by said actuating elements, means for producing a digital signal corresponding to the level or frequency of the test tone, a digital electronic memory including a write input or an information input allocated to each test station and controlled by the respective actuating element of its test station to control the passage of said digital signal into said memory via the information and/or the address inputs of the memory, and an output device connected to read-out the signals stored in the digital memory.

2. An audiometer system as claimed in claim 1 further comprising switching means for interrupting the passage of said test tones to the test stations, and gating means operative so that any time after the presentation time of a test tone and before the beginning of the next test tone the write input of the digital memory may be blocked.

3. An audiometer system for recording audiometric data comprising, means for automatically generating a series of test tones of predetermined duration, different frequencies and/or different levels in accordance with a program, one or more test stations each of which comprise a reproducing device and an actuating element for recording the test tones which have been perceived, a digital electronic memory including a write input or an information input allocated to each test station with said write or information input being controlled by the actuating element of its respective test station, means for applying a digital signal corresponding to the level or the frequency of the test tone to the information and/or the address inputs of the memory, an output device connected to read-out the signals stored in the digital memory, a microphone for measuring extraneous sound in a test room, means for deriving a signal which corresponds to the average value of the microphone signal level during the presentation time of the test tone, and means for repeating the test tone depending on the difference in level between the extraneous sound measured and the test tone.

4. An audiometer system as claimed in claim 3 further comprising, means for forming a signal corresponding to the average level of the microphone signal level occurring outside the test tone presentation time, and means for effectively inhibiting the test tone until the difference in levels between the extraneous sound and the test tone drops below a predetermined value.

5. An audiometer system for recording audiometric data comprising, means for automatically generating a series of test tones of predetermined duration, different frequencies and/or different levels in accordance with a program, one or more test stations each of which comprise a reproducing device and an actuating element for recording the test tones which have been perceived, a digital electronic memory including a write input or an information input allocated to each test station with said write or information input being controlled by the actuating element of its respective test station, means for applying a digital signal corresponding to the level or the frequency of the test tone to the information and/or the address inputs of the memory, an output device connected to read-out the signals stored in the digital memory, a microphone for measuring extraneous sound in a test room, means for forming a signal which corresponds to the average value of the microphone signal level occurring outside the presentation time of the test tone, and means for inhibiting the test tone until the difference in level between the extraneous sound and the test tone has dropped below a predetermined value.

6. An audiometer system for recording data for a plurality of test stations comprising, a program control unit for generating program control signals, each test station including a manually operable actuating element operable by a test subject in accordance with perceived test tones, means common to said plurality of test stations and responsive to said program control signals for generating a series of test tones of predetermined duration and whose frequency and/or level is adjustable as a function of the program control signals, a digital electronic memory means including a plurality of control inputs each allocated to a respective test station and responsive to its respective test station actuating element to control the storage of data signals in the memory means relating to the frequency and level of said test tones, said digital memory means further comprising first and second input means coupled to the program control unit to receive electric data signals corresponding to the frequency and level of the test tones for storage in the memory means under the control of said plurality of control inputs, and an output device coupled to the digital memory means to read out the data signals stored therein.

7. An audiometer system as claimed in claim 6 wherein each test station includes a sound reproducing device and said test tone generating means operates independent of said actuating elements.

8. An audiometer system as claimed in claim 6 further comprising gating means under control of the program control unit and interposed in circuit between said actuating elements and the control inputs of the digital memory means.

9. An audiometer system as claimed in claim 6 further comprising a converter interposed in circuit between the output of the program control unit and said test tone generating means, and said test tone generating means includes, in cascade, a frequency adjustable oscillator whose frequency is controlled by the program control unit via the converter and a variable gain amplifier whose output level also is controlled by the program control unit via the converter, said system further comprising switching means controlled by the converter and connected in circuit between the amplifier output and said plurality of test stations for periodically interrupting the test tone signals thereby to generate said series of test tones of predetermined duration.

10. An audiometer system as claimed in claim 6 further comprising means for producing a signal corresponding to the extraneous noise level at a test station, and means for effectively inhibiting a test tone as a function of the relative levels of the noise signal and the test tone signal.

11. An audiometer system as claimed in claim 1 further comprising a counter responsive to said actuating elements for causing, for each test station, the storage of control instruction signals received from the respective actuating elements at different address locations in the digital memory means in the event the actuating elements are not actuated by the respective patients within a predetermined time interval.

* * * * *